US012590198B2

(12) United States Patent
Bettinger

(10) Patent No.: US 12,590,198 B2
(45) Date of Patent: Mar. 31, 2026

(54) PROCESS FOR THE DECOMPOSITION OF POLYURETHANE

(71) Applicant: NEVEON GERMANY GMBH, Wiesbaden (DE)

(72) Inventor: Herbert Bettinger, St. Wendel (DE)

(73) Assignee: Neveon Germany GMBH, Wiesbaden (DE)

( * ) Notice: Subject to any disclaimer, the term of this patent is extended or adjusted under 35 U.S.C. 154(b) by 494 days.

(21) Appl. No.: 18/039,167

(22) PCT Filed: Nov. 29, 2021

(86) PCT No.: PCT/EP2021/083434
§ 371 (c)(1),
(2) Date: May 26, 2023

(87) PCT Pub. No.: WO2022/112581
PCT Pub. Date: Jun. 2, 2022

(65) Prior Publication Data

US 2024/0301161 A1 Sep. 12, 2024

(30) Foreign Application Priority Data

Nov. 27, 2020 (DE) ..................... 10 2020 131 581.3

(51) Int. Cl.

| | |
|---|---|
| ***C08J 11/24*** | (2006.01) |
| ***C07C 209/62*** | (2006.01) |
| ***C07C 263/04*** | (2006.01) |
| ***C08J 11/14*** | (2006.01) |
| ***C08J 11/28*** | (2006.01) |

(52) U.S. Cl.
CPC ............. *C08J 11/28* (2013.01); *C07C 209/62* (2013.01); *C07C 263/04* (2013.01); *C08J 11/14* (2013.01); *C08J 2375/04* (2013.01)

(58) Field of Classification Search
CPC ......... C08J 11/14; C08J 11/28; C07C 209/44; C07C 209/62
See application file for complete search history.

(56) References Cited

U.S. PATENT DOCUMENTS

| | | | |
|---|---|---|---|
| 4,196,148 | A | 4/1980 | Mahoney |
| 5,208,379 | A | 5/1993 | Yang et al. |

FOREIGN PATENT DOCUMENTS

| | | |
|---|---|---|
| DE | 3037545 C2 | 10/1979 |

OTHER PUBLICATIONS

International Search Report for PCT/EP2021/083434 dated Mar. 17, 2022.
Motokucho Suguru et al., "Hydrolysis of aromatic polyurethane in water under high pressure of CO2", Journal of Polymer Science Part A: Polymer Chemistry, US, vol. 55, No. 12, Jun. 15, 2017 (Jun. 15, 2017), pp. 2004-2010, retrieved from the Internet: https://api.wiley.com/onlinelibrary/tdm/vl/articles/10.1002%2Fpola28576.
Mir Mohammad Alavi Nikje et al., "Polyurethane Waste Reduction and Recycling: From Bench to Pilot Scales", Designed Monomers and Polymers, vol. 14, No. 5, Jan. 1, 2011 (Jan. 1, 2011), pp. 395-421.
Pruefungsbescheid (Examination notice) POSTANSCHRIFT Deuisches Patent. und Markenamt . 80297 München dated Oct. 29, 2021.

*Primary Examiner* — Sikarl A Witherspoon
(74) *Attorney, Agent, or Firm* — Moser Taboada

(57) ABSTRACT

The invention relates to a method for decomposing polyurethane, wherein material containing polyurethane is heated to a temperature from 190° C. to 250° C. under overpressure in the presence of an aqueous solution containing 1 to 45 mass percent urea. It further relates to a liquid process medium obtainable thereby.

11 Claims, 3 Drawing Sheets

PROCESS FOR THE DECOMPOSITION OF POLYURETHANE

The invention relates to a method for decomposing polyurethane and a process medium obtainable with this method.

Because of their many adjustable properties, polyurethanes are used for a wide range of products in both industrial and domestic applications. Examples of such products include foams, paints, adhesives, pourable sealing compounds, hoses, seals, floor coverings, mattresses, car parts, parts for sports equipment, parts for shoes and the like.

Accordingly, a correspondingly high proportion of polyurethane waste products are created when these products are damaged or reach the end of their service life.

In the past, therefore, various solutions have been suggested for reconditioning polyurethane waste products. A number of patents relate to methods in which polyurethane waste products are dissolved in aliphatic diols, for example U.S. Pat. Nos. 4,044,04, 3,632,530 and 4,162,995, as well as the German unexamined patent application 2304444. U.S. Pat. No. 4,316,992 suggests dissolution in high-boiling saturated alcohol, and U.S. Pat. No. 4,039,568 suggests dissolving in the presence of various alcoholates. The disadvantage in all of these methods is the fact that hydrocarbons in the form of diols are needed for the process.

The problem addressed by the invention consists in providing alternative solutions, in which substances preferably with less adverse environmental impact are used.

The invention ensues from the features of the independent claims. Advantageous further refinements and variants are the objects of the dependent claims.

The problem is solved in a first aspect by a method for decomposing polyurethane, wherein material containing polyurethane is heated to a temperature from 190° C. to 250° C. under overpressure in the presence of an aqueous solution containing 1 to 45 mass percent urea. At the beginning of the method, polyurethane-containing material is present in or together with the aqueous, urea-containing solution.

After the chosen treatment period has ended, the polyurethane fraction of the polyurethane-containing material, which was originally in solid form has been partially or completely converted into substances in a liquid process medium, which is attributable to the aqueous solution containing urea that was present at the start of the process. The process medium may also contain further solids, for example solids that were embedded in the solid polyurethane or adsorbed thereon, or plastics other than polyurethane. The liquid process medium contains products of decomposition and/or other secondary products that are a result of the originally present polyurethane. The conversion into the liquid process medium advantageously provides the capability to convert originally solid polyurethane into a form that is more easily manageable, and under certain circumstances to isolate reusable materials from the liquid process medium obtained, or to include them to usefully in further reactions.

The term overpressure is understood to mean any pressure greater than atmospheric ambient pressure. According to one variant, heating is carried out at a pressure from 1.05 bar to 100 bar. Examples of pressure ranges are 10 bar to 45 bar, for example 12 bar to 40 bar, or 25 bar to 35 bar. For the purpose of simple process management, the overpressure is an equilibrium pressure that is adjusted automatically upon heating, for example the equilibrium pressure that is created when heating in a pressure vessel.

The method is preferably completed with a period from 20 minutes to 240 minutes, in particular 45 minutes to 240 minutes, 90 minutes to 240 minutes, for example 120 minutes up to 240 minutes. An example of a preferred period is the period from 30 minutes to 180 minutes, for example the period between 40 minutes and 180 minutes (40 minutes to 180 minutes). In this context, the reaction temperature may remain constant at a value within the specified temperature range, or it may have various values within the specified temperature range, in order to reach a predetermined target value through temperature regulation, for example. The period is preferably a single continuous period, but it may also be made up cumulatively from separate periods in which the intended temperature conditions are maintained. In the course of extensive experiments, it was found that first indications of the formation of solids occurred at a temperature of 245° C. and a period of 240 minutes. Taking into account a preset duration of 240 min for the heat treatment, a temperature of 250° C. is therefore considered to be the practicable upper limit for the temperature.

With this method, it becomes possible to effect the decomposition of polyurethane using urea, which is to say a substance that occurs naturally in the environment, and is accordingly also naturally degradable.

The polyurethane-containing material may be material which, in addition to the polyurethane and separately therefrom, contains a non-polyurethane component, for example polyurethane in combination with a component from another plastic, such as particles of styrene-acrylonitrile, a component consisting of a metal, a component consisting of a glass, or a component consisting of an inorganic material, for example calcium carbonate. Non-limiting examples of such include polyurethane objects that contain fixing elements of metal, or composite materials of polyurethane and another plastic, for example refrigerator parts containing polyurethane as a heat insulating layer and other plastics as a resist coating. However, polyurethane-containing material may also be understood to mean material that consists entirely of polyurethane. The polyurethane itself may be pure polyurethane or a polyurethane that contains other substances, for example plasticisers, microbicides, antioxidants, stabilisers, against UV light for example, flame retardants, dyes or polymerisation initiator residues. The term "polyurethane-containing material" may also refer to a mixture of various polyurethane-containing materials, for example materials, that each contain different types of polyurethane.

The decomposition of the polyurethane may be carried out partially, or it may also pass through intermediate stages depending on selected process parameters in which the polyurethane exists in reduced form until the complete decomposition of the polyurethane contained in the material, so that the polyurethane no longer exists as a solid.

The term polyurethane according to the standard technical definition thereof is understood to be a polymer which includes as its characteristic group the urethane group according to the following formula (I):

(I)

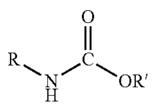

Polyurethanes can generally by obtained by the polyaddition of divalent or higher-valent alcohols with formula (II)

$$HO—R'—OH \quad (II),$$

wherein R' stands for a low-molecular or even an already polymeric aliphatic or aromatic radical, optionally comprising at least one further hydroxyl group, with diisocyanates having the general formula (III)

$$O{=}C{=}N{-}R{-}N{=}C{=}O \qquad \text{(III)},$$

wherein R has the same meaning as R'.

The chemistry and technical manufacture and processing of polyurethanes are generally known to the person skilled in the art, and described for example in in Ullmann's Encyclopedia of Industrial Chemistry, 6th Completely Revised Edition, Wiley-VHC Verlag GmbH & Co. KGaA, Weinheim, Germany, 2003, Volume 28, Pages 667-722. Most of the polyurethane foams (also referred to in the following as PUR-foams) are produced on the basis of aromatic isocyanates. The most important representatives of this group are mixtures of the isomers 2,4-toluene diisocyanate and 2,6-toluene diisocyanate (TDI), and mixtures of isomers of diphenylmethane diisocyanate (MDI), of which diphenylmethane-2,2'-diisocyanate (2,2'-MDI), diphenylmethane-2,4'-diisocyanate (2,4'-MDI) and diphenylmethane-4,4'-diisocyanate (4,4'-MDI) may be cited as non-limiting example, and prepolymerised MDI. TDI 80 is the most important diisocyanate in soft foam production. TDI 65 is used in many soft foams, also particularly in ester foams. In the two designations, the numbers 80 and 65 stand for percentage by mass of the highly reactive isomer 2,4-toluene diisocyanate, the remainder up to 100 percent by mass is supplied by the isomer 2,6-toluene diisocyanate. Polyether, polyester or diamines are used for preference as polyol components. The properties may also be modified further by the addition of stabilisers such as silicon-polyether copolymers, epoxies, benzophenone and other substances. The properties of the foam may also be varied by additives. Thus for example phosphoric acid ester is used as a flame retardant. Mechanical reinforcing agents such as carbon fibres may also be incorporated in the foams, and these represent examples of non-polyurethanes, which may be contained in the polyurethane-containing material as further components. Filler materials such as calcium carbonate may also be used.

The polyurethane may be polyurethane foam or nonporous polyurethane, wherein non-limiting examples of nonporous polyurethane are polyurethane hoses or polyurethane sealing compounds.

According to a particular variant of the method, the polyurethane (PUR) comprises polyurethane soft foam (PUR soft foam), polyurethane hard foam (PUR hard foam), light shredder residue or a mixture of two or more representatives thereof, or particularly consists thereof. The term light shredder residue is known to the person skilled in the art, and generally describes a heterogeneous mixture which may consist of various plastics, organic and inorganic materials, wherein the actual composition depends on the nature of the shredded scrap. An example of a light shredder residue is produced when recycling refrigerators in which the foam filling of cavities consists of PUR hard foam, optionally with the addition of other plastics, for example plastics originating from cable passthroughs. Light shredder residue from refrigerator recycling may further contain mineral fractions, due to filler materials contained in the polyurethane, for instance.

Non-limiting examples of sources of polyurethane-containing material are waste from production in the mattress industry, the automotive industry, the building industry, the furniture making industry, the footwear industry, the electronics industry and the sport/leisure industry, and/or defective or no longer used products of said industries, such as mattresses; bodywork or other vehicle parts such as bumpers, instrument panels, head supports, armrests, or carpets; wall panels or pipe insulations; furniture or furniture parts; shoes or shoe parts, for example soles or toecaps; cable sheathing, plugs, power strips or parts thereof; or sports equipment such as snowboards or roller skate wheels.

For the purposes of the method according to the invention, the following may be used as polyurethane-containing material: in particular polyurethane foams (hereinafter also referred to as PUR foams), selected in the following compositions: PUR soft foams based on non-reactive polyether polyols ("standard polyether polyols") having molecular weights in the order of 3000 g/Mol, filled (with SAN copolymers, i.e. styrene-acrylonitrile copolymers) or unfilled; PUR soft foams based on reactive high resilience polyether polyols with molecular weights greater than 3000 g/Mol, filled (with SAN copolymers or PHD, i.e. polyurea dispersion) or unfilled; PUR soft foams based on reactive 6-function polyether polyols; PUR soft foams based on hypersoft polyether polyols; PUR soft foams based on polyether polyols and mixtures thereof that serve as precursors for viscoelastic foams and may also PEG (polyethylene glycol) as a component; PUR soft foams based on polyester polyols, filled or unfilled; PUR soft foams based on abovementioned polyol mixtures in combination with TDI or MDI; and PUR hard or semi-hard foams based on abovementioned polyol mixtures in combination with TDI or MDI, and hard integral foams consisting of the abovementioned components.

According to particular further developments, the PUR foams comprise one or more representatives of the product family of soft foams and/or one or more representatives of the product family of hard foams.

Soft foams comprise plastics such as standard polyether foams, high resilience polyether foams, combustion modified polyether foams (CME), combustion modified high resilience polyether foams (CMHR), viscoelastic polyether foams and polyester foams. Exemplary compositions are known to the person skilled in the art, and are described for example in Documents DE 3630225 C2, U.S. Pat. No. 3,905,924 and DE 10 2007 051 089 A1.

These soft foams preferably include the following components, or consist of combinations of two or more representatives thereof:

Isocyanates:

- 2,4- and/or 2,6-toluylene diisocyanate (TDI) and any mixtures of these isomers;
- 4,4'- and/or 2,2'-diphenylmethane diisocyanate (MDI) and any mixtures of these isomers;
- Polymer MDI ("raw" MDI) and MDI prepolymerised with polyvalent polyols (preferably di- and/or trivalent polyethers); and/or
- any mixtures of TDI and MDI from abovementioned isomers and formations.

Polyols:

Polyether polyols and/or polyester polyols such as known per se for producing cellular and homogeneous polyurethane foams, and are described for example in DE-A 2 832 253 (pages 11-18).

The following are cited as examples here:

- (Standard) polyethers with hydroxyl groups (functionalities) of preferably 2 and 3;
- (Standard) polyethers with hydroxyl groups (functionalities) of preferably 2 and 3 filled with SAN (styrene acrylonitrile) solid;

- Hypersoft polyethers with functionalities of preferably 3; Reactive polyethers with primary hydroxyl groups preferably with functionalities of 3, 5 and 6;
- Reactive polyethers with primary hydroxyl groups filled with SAN (styrene acrylonitrile) solid or PHD (polyurea dispersion) with a functionality of 3;
- Reactive polyols prepolymerised with TDI, preferably with a functionality of 3;
- Non-reactive polyols prepolymerised with TDI, also known in the technical community as "quasi-prepolymers" (QPP), preferably with a functionality of 3, in which the polyols are present in greater quantity than the TDI;
- Polyols based on renewable raw materials and different functionalities.

Natural oil products with a different number of hydroxyl groups, wherein castor oil may be cited as a non-limiting example;

Compounds with amino groups or hydroxyl groups, which function as chain extenders or crosslinking agents and typically have 2 to 8, preferably 2 to 4 hydrogen atoms capable of reacting with isocyanates, for example diethanolamine, triethanolamine, diisopropanolamine, sorbitol, glycerin and urea.

As with the hard foams that will be listed below, these soft foams comprised optionally one or more additional substances, selected from:

Catalysts of the type known per se, such as tertiary amines and reactive (integrable) amines; tin (II) compounds and zinc compounds, surfactant additives such as emulsifiers, foam stabilisers, flame retardants, sorbitol, glycerin, diamines, urea, tertiary amines, and siloxane-based or non-siloxane based stabilisers.

The hard foams of this particular further development can be found for example in products such as insulating panels (also as sandwich elements with various covering layers), in-situ foams, spray-applied foams, foams produced with the overlay process, foams for solar panel filler materials, foams for pipe insulations, filling and expanding foams, and block foams. The compounds are familiar enough to the person skilled in the art, and are described comprehensively in Document EP 0 318 784 A2, for example.

The hard foams preferably comprise the following components or consist of combinations of two or more representatives thereof:

Isocyanates:

- 2,4- and/or 2,6-toluylene diisocyanate (TDI) and any mixtures of these isomers;
- 4,4'- and/or 2,2'-diphenylmethane diisocyanate (MDI) and any mixtures of these isomers;
- Polymer MDI ("raw" MDI) and MDI prepolymerised with polyvalent polyols (preferably di- and/or trivalent polyethers);
- any mixtures of TDI and MDI from abovementioned isomers and formations, but preferably polymer MDI (raw MDI).

Besides foams, further examples of polyurethane in the polyurethane-containing material are polyurethane elastomers and polyurethane duroplasts.

The method according to the invention may be carried out discontinuously, continuously or semi-continuously.

In the discontinuous method, also known as the batch method, the feedstock is introduced into a reaction vessel, exposed to the reaction conditions, and the reaction product is then removed after the end of the treatment period. After this, the reaction vessel is charged with a fresh batch of feedstock.

In the continuous method, polyurethane-containing material and urea-containing aqueous solution is fed into the reaction vessel not just once before the start of the reaction, but continuously. Similarly, liquid process medium is also removed continuously. Usually, infeed and removal take place at different in places, particular the polyurethane-containing material together with the urea-containing aqueous solution may be pushed or transported via active conveying means within the reaction vessel from the infeed point to the removal point. Accordingly, there is a low degree of decomposition in regions close to the infeed point, wherein the polyurethane-containing material migrates or is conveyed to the removal point together with the urea-containing aqueous solution, and exhibits a greater degree of decomposition relative to the polyurethane as it comes closer to the removal point.

Semicontinuous methods represent any possible transitional form between the two methods described previously. For example, the liquid process medium may not be removed substantially completely after the end of a discontinuous method. As a further example, in a variation of a continuous method, fresh polyurethane-containing material and/or urea-containing aqueous solution may not be fed in continuously, so that fresh polyurethane-containing material and/or urea-containing aqueous solution is not being fed in at all times, but rather only at certain times, for example periodically, or when a certain degree of decomposition of the polyurethane in the reaction vessel is observed.

Any kind of apparatus commonly used in the field may serve as a reaction vessel, or may easily be adapted by the person skilled in the art for the purposes of the method according to the invention. Examples of such are pressure vessels or pressure reactors that are designed for batch filling and have capacity for reaction volumes from a laboratory scale, for example 0.1 to 10 litres through intermediate ranges from 10 litres to 1 cubic metre up to a large industrial sale in the range from 1 cubic metre to dozens or hundreds of cubic metres. Alternatively, the pressure vessels or pressure reactors may be designed for continuous or semicontinuous operation, and may include pressure locks for feeding in the polyurethane-containing material and/or removing the liquid process medium.

The polyurethane-containing material may be introduced in unreduced form. For example, a polyurethane foam may be wetted with the urea-containing aqueous solution, or completely saturated therewith, and then heated to the temperature in the range from 190° C. to 250° C.

However, the polyurethane-containing material is preferably introduced in the reduced state. For this process, standard technical comminution practices can be implemented, for example the polyurethane-containing material may be cut, torn, grated into flakes, shredded, granulated, ground or pulverised, optionally after a prior temperature reduction to increase its frangibility. Non-limiting examples of the size of the comminution products obtained in this way are about 0.5 $cm^3$ to 10 $cm^3$ (0.5 ml to 10 ml), such as about 1 $cm^3$ to 5 $cm^3$, in particular for polyurethane-containing material that is porous or has a large surface area, or comminution products with a diameter, measured at the widest point, not exceeding about 10, 5, 2, 1, 0.5, 0.1, 0.05 or 0.01 millimetres. The comminution may be carried out in the reaction vessel while the method is in progress using corresponding apparatuses, although the reaction vessel is preferably filled with polyurethane-containing material already in comminuted form. If the polyurethane-containing material is not merely wetted with the urea-containing solution, but is completely absorbed therein, the resulting substance is substantially a suspension of the polyurethane-containing material in the urea-containing aqueous solution.

Relative to the total mass of the aqueous solution, the urea constitutes a fraction in the aqueous solution of 1 to 45 mass percent, in particular 1 to 20 mass percent, for example 1 to 10 mass percent, such as for example 1 to 7 mass percent, for example 1.5 to 5 mass percent, 1.5 to 4 mass percent, 2 to 4 mass percent, 2.5 to 3.5 mass percent, or 3 mass percent. Examples of further ranges or further concentrations are 5 to 10 mass percent, 1 mass percent, 5 mass percent, 7.5 mass percent and 10 mass percent. Preferable from the point of view of the ratio between the quantity of urea for use and the degree of polyurethane decomposition achieved is a range between 1 mass percent and 10 mass percent, for example 2.5 to 10 mass percent, 2 mass percent to 7.5 mass percent, such as about 3 mass percent to 5 mass percent.

The method is preferably performed in the exclusion of air, wherein optionally small residual quantities of air, for example 20% or 10% of the volume of the reaction vessel in which the decomposition process is carried out, are permissible, or is performed in the absence of air, or in the presence of an inert gas, for example nitrogen gas. The method is preferably carried out in the presence of an inert gas.

In a particular variant, the aqueous solution comprises 2.5 to 10 mass percent urea, and heating is carried out over a period from 45 to 250 minutes, in particular over a period from 45 to 240 minutes.

According to one variant, the ratio between urea-containing aqueous solution and polyurethane-containing material is 0.2 ml/g to 5 ml/g, such as about 0.4 ml/g to 5 ml/g, for example 0.2 ml/g to 2.5 ml/g, 0.2 ml/g to 2.0 ml/g, 0.2 ml/g to 1.7 ml/g, 0.2 ml/g to 1.2 ml/g or 0.2 ml/g to 1.0 ml/g, or for example 0.4 ml/g to 2.5 ml/g, 0.4 ml/g to 2.0 ml/g, 0.4 ml/g to 1.7 ml/g, 0.4 ml/g to 1.2 ml/g or 0.4 ml/g to 1.0 ml/g. Particularly when the ratio between the volume of urea-containing aqueous solution and the quantity of polyurethane processed therewith is low, this allows efficient use of the volume available for carrying out the decomposition method. With regard to use with polyurethane-foam, a quantity of 0.2 ml/g, in particular 0.25 ml/g, in particular 0.29 ml/g, and in particular 0.4 ml/g represents a lower limit, at which the polyurethane foam is still sufficiently moistened with the aqueous urea-containing solution to enable the desired decomposition of polyurethane.

In the context of the method, it is provided optionally as a further process step to recover at least some of the liquid process medium obtained after heating. Accordingly, the liquid process medium is partially or completely removed from the reaction vessel. This makes it available for further optional steps subsequently, for example for fractionation into individual substances or substance groups, which can be disposed of more selectively, or in the best case, are available as sources of raw material.

According to one variant, it is provided that solids contained in the recovered liquid process medium are removed therefrom, if such are contained in it. These may be for example metal parts, particles of other plastics, or particulate products of the reaction or decomposition of the polyurethanes or polyurethane components. Methods for removing solids are known to the person skilled in the art and include for example sedimentation, centrifugation or filtration.

According to a preferred variant, the 1 to 45 mass percent urea-containing aqueous solution is free from polyols, for example free from diols, and/or free from carboxylic acids and/or free from ammonia. This helps advantageously to avoid environmentally harmful substances. According to a particular variant, the aqueous solution consists of water and 1 to 45 mass percent urea.

In the course of the decomposition method, the polyurethane is converted partially or completely into the liquid process medium. Accordingly, polyurethane-containing materials that were originally in solid form, which may have a high volume requirement—particularly in the case that the polyurethane is in the form of a foam—can be converted into more easily processable liquids, namely the liquid process medium, with a lower volume requirement. The possibility also exists to fractionate the substances contained in the liquid process medium and/or to isolate them and/or optionally to deliver them for further use or reuse.

The present invention accordingly relates to a process medium that is or can be obtained via a method described herein. It relates in particular to a process medium of such kind containing polyols that were used to produce the polyurethane that was decomposed by means of the method, or containing modifications of such polyols, and/or containing diamines or modifications of such diamines, wherein the diamines represent precursors of the di-isocyanates that were used to produce the polyurethane that was decomposed by means of the method.

Non-limiting examples of modifications are ring formations or deaminations. A process medium of such kind thus contains valuable raw materials for the chemical industry, in particular for the polyurethane recycling economy, which can be used again, possibly after they have been isolated from the process medium.

Further advantages, features and particularities are discernible from the following description, in which—optionally with reference to the figures—at least one exemplary embodiment is described in detail.

EXAMPLE 1—POLYURETHANE SOFT FOAMS

Figure 1:
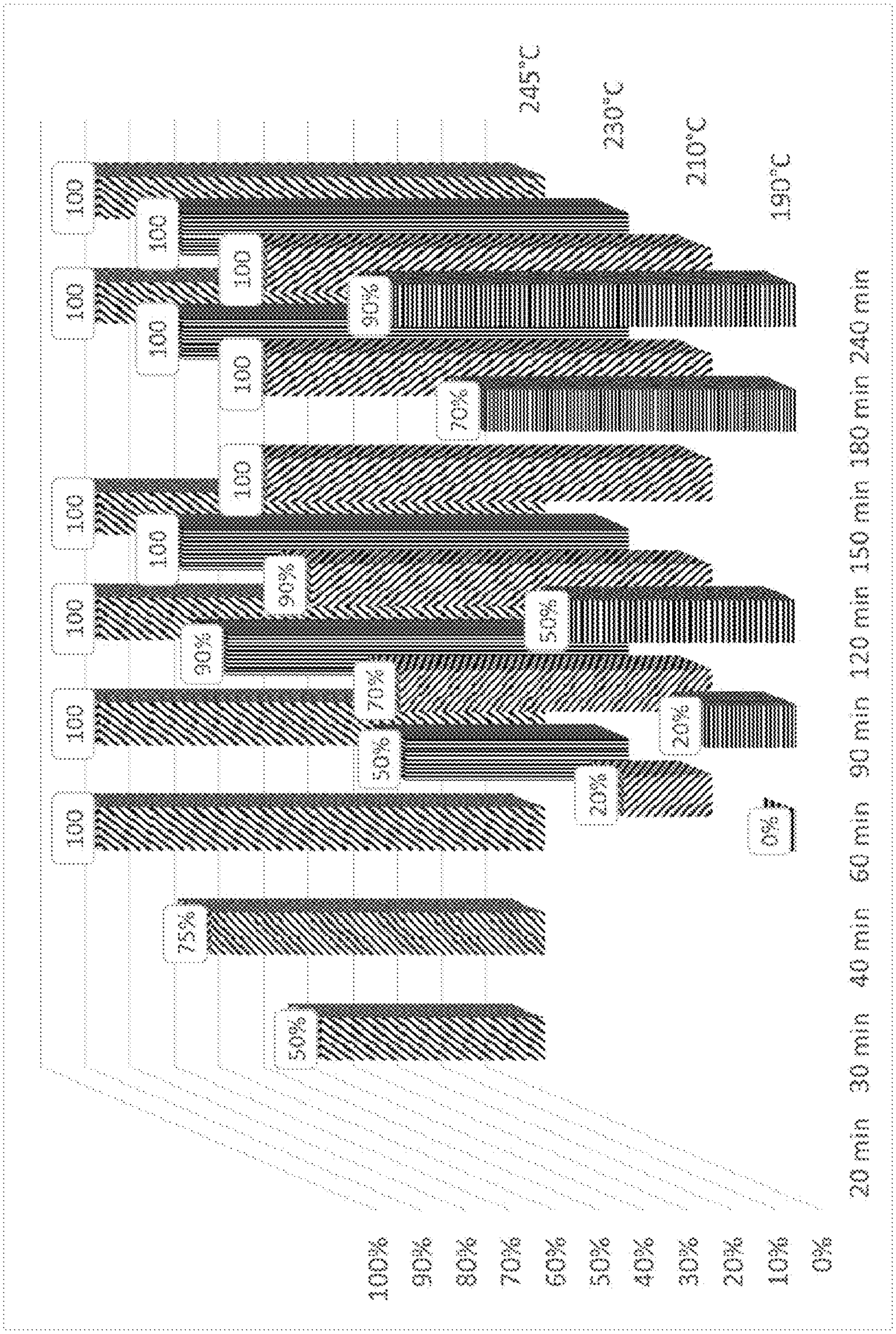
FIG. 1 shows a three-dimensional chart representing the degree of decomposition of polyurethane-containing material as a function of temperature and period for which the method is carried out.

Two polyurethane soft foams with TDI base or MDI base (Product designations: R 4030 and R 5535, Source: Eurofoam Deutschland GmbH Schaumstoffe, Wiesbaden, Deutschland) weighing 20.0 g and 19.6 g respectively were absorbed respectively in 32.2 ml and 35.7 ml 7.5-% urea solution, and treated for 180 minutes at 190° C. in a closed pressure vessel.

TABLE 1

| Initial weight of polyurethane soft foam sample [g] | Urea content of the aqueous solution [mass %] | Volume of aqueous solution used [ml] | Decomposition [%] |
|---|---|---|---|
| 20.0 (R 4030) | 7.5 | 32.2 | 50 |
| 19.6 (R 5535) | 7.5 | 35.7 | 90 |

180 min at 190° C.

The samples taken were allowed to cool, and then classified semi-quantitatively by visual assessment of the degree of decomposition of solid polyurethane, and corresponding disappearance of observable solid material and conversion into the liquid process medium, wherein (as in all other subsequent experiments) "0%" signifies that no decomposition of polyurethane had yet taken place, and accordingly the quantity of solid polyurethane originally used was still present in its entirety, while "100%" stands for complete decomposition and corresponding conversion of the polyurethane into the liquid process medium.

In both cases, partial decomposition took place, wherein differing quantities of solids were still present in the liquid process medium in the form of evidently condensed foam residues.

EXAMPLE 2—POLYURETHANE INTEGRAL FOAM

Two samples of flexible polyurethane integral foam, one with ether base and one cast elastomer marketed under the brand name Colo-Fast® (BASF, SE, Ludwigshafen, German) originally weighing 25 g and 35 g respectively were absorbed in 40 ml 3% urea solution, and treated for 240 minutes at 245° C. in a closed pressure vessel filled to 80% capacity.

TABLE 2

| Initial weight of polyurethane integral foam sample [g] | Urea content of the aqueous solution [mass percent] | Volume of aqueous solution used [ml] | Decomposition [%] |
|---|---|---|---|
| 25 (Ether base) | 3 | 40 | 100 |
| 35 (Colo-Fast) | 3 | 40 | 100 |

240 min at 245° C.

Complete decomposition of the polyurethane-material used took place, although a small fraction of particles was observed, possibly attributable to polymerisation.

EXAMPLE 3—NON-FOAMED POLYURETHANE

Solid, non-foamed polyurethanes were used in series of tests for the decomposition method. For these tests, blue plastic polyurethane hoses of type "PUN" (Festo Gesellschaft m.b.H, Vienna, Austria) were comminuted, and 1 g of each was heated to 210° C. in 25 ml of an aqueous urea solution with a urea content of 1 mass percent, 5 mass percent, 7.5 mass percent and 10 mass percent in a closed pressure vessel for a period of 150 minutes.

The test series served essentially to determine the influence of the urea concentration and to calculate the decomposability of solid polyurethanes.

TABLE 3

| Initial weight of polyurethane hose sample [g] | Urea content of the aqueous solution [mass percent] | Volume of aqueous solution used [ml] | Decomposition [%] |
|---|---|---|---|
| 30 | 1 | 25 | 100 |
| 30 | 5 | 25 | 100 |
| 5 | 7.5 | 20 | 100 |
| 5 | 7.5 | 20 | 100 |
| 30 | 7.5 | 25 | 100 |
| 30 | 10 | 25 | 100 |

150 min at 210° C.

As a result, it was found that no fractions of the originally used solid polyurethane were observable in any of the samples. Thus, non-foamed polyurethanes are decomposable under the stated experimental conditions.

EXAMPLE 4—DUROPLASTIC POLYURETHANE

As a further example of non-foamed polyurethanes, a duroplast polyurethane core with a volume weight of 165 g/l, as is used in skis, was used for the decomposition method. The core was comminuted, and 15 g thereof in 40 ml of an aqueous urea solution with a urea content of 3 mass percent was heated to 210° C. for a period of 150 minutes in a closed pressure vessel with fill volume of 80% of the available capacity (remaining volume 20%: air).

TABLE 4

| Initial weight of polyurethane ski core material sample [g] | Urea content of the aqueous solution [mass percent] | Volume of the aqueous solution used [ml] | Decomposition [%] |
|---|---|---|---|
| 15 | 3 | 40 | 100 |

150 min at 210° C.

As a result, it was found that no fractions of the originally used non-foamed polyurethane were observable any longer in the liquid phase obtained.

EXAMPLE 5—ELASTOMERIC POLYURETHANES

As examples of elastomeric polyurethanes, springs made of microcellular polyurethane, which are marketed under the brand name Cellasto® (BASF, SE, Ludwigshafen, Germany), and the cast elastomer Colo-Fast® (BASF SE, Ludwigshafen, Germany) were used. The samples were comminuted and heated to 210° C. in separate lots in 40 ml of an aqueous urea solution with a urea content of 3 mass percent for a period of 150 minutes in a closed pressure vessel with fill volume of 80% of the available capacity (remaining volume 20%: air).

TABLE 5

| content | | | |
|---|---|---|---|
| Initial weight of elastomeric polyurethane sample [g] | Urea content of the aqueous solution [mass percent] | Volume of aqueous solution used [ml] | Decomposition [%] |
| 35 (Cellasto ® (sample 1) | 3 | 40 | 100 |
| 40 (Cellasto ® (sample 2) | 3 | 40 | 100 |
| 35 (Colo-Fast ®) | 3 | 40 | 100 |

150 min at 210° C.

As a result, it was found that no fractions of the originally used elastomeric polyurethane were observable any longer in the liquid phase obtained.

EXAMPLE 6—TIME SERIES

In a test series, the R 4030 and R 5535 polyurethane foams described previously were heated in an aqueous urea solution with a urea content of 7.5 mass percent at a temperature of 230° C. in a closed pressure vessel for 60 minutes, 90 minutes or 120 minutes.

TABLE 6

| Initial weight of polyurethane foam sample [g] | Urea content of the aqueous solution [mass %] | Volume of aqueous solution used [ml] | Duration [min] | Decomposition [%] |
|---|---|---|---|---|
| 9.98 (R 4030) | 7.5 | 25 | 60 | 50 |
| 10.47 (R 5535) | 7.5 | 25 | 60 | 50 |
| 9.93 (R 4030) | 7.5 | 25 | 60 | 50 |
| 10.36 (R 5535) | 7.5 | 25 | 60 | 50 |
| 10.08 (R 4030) | 7.5 | 25 | 90 | 90 |
| 10.04 (R 5535) | 7.5 | 25 | 90 | 90 |
| 10.15 (R 4030) | 7.5 | 25 | 120 | 100 |
| 10.23 (R 5535) | 7.5 | 25 | 120 | 100 |

Various periods at 230° C.

At the decomposition rate classified as 50%, the foam structures were transformed into a solution, resulting in a paste-like consistency, at the decomposition rate classified as 90%, the foam structure was almost completely liquefied, at 100 percent decomposition, it was entirely liquefied.

EXAMPLE 7—TIME SERIES AND TEMPERATURE SERIES

Given that the preceding experiments had shown that in principle any type of polyurethane-containing material can be decomposed with the method, in a new series of experiments with the aim of making a systematic calculation of a temperature-dependency and time-dependency of the decomposition, a mixture of different polyurethane-containing materials was used, specifically a mixture of identical proportions by weight, each having an original weight of 4.15 g.

a) Standard foam grade TDI 80-based with filler material (calcium carbonate) and SAN polymer particles (N 4045 WS),
b) High resilience (HR) polyurethane foam grade TDI 80/TDI65-based with filler material (calcium carbonate) and SAN polymer particles (R 4040 WS),
c) High resilience (HR) polyurethane foam grade MDI-based with filler material (calcium carbonate) and SAN polymer particles (R 5535 WS), and
d) Viscoelastic foam grade MDI-based-V5018 WS, Eurofoam Deutschland GmbH Schaumstoffe) with no filler materials.

The polyurethane-containing material obtained in this way was reacted in shredded form with a 3% urea solution in a ratio of 0.582 ml urea solution per gram of polyurethane-containing material. In order to run the temperature series, samples in closed pressure vessels with an equilibrium pressure set were heated to 190° C., 210° C., 230° C. and 245° C. in a heat cabinet, and were removed after a residence time of 60 minutes, 90 minutes, 120 minutes, 180 minutes and 240 minutes at the respective temperature. Three samples were tested and evaluated in parallel for each time point.

The samples that were removed were allowed to cool and then classified semi-quantitatively by visual assessment to obtain an average value for each set of three samples, with regard to the degree of decomposition of solid polyurethane and the corresponding disappearance of observable solid material and conversion to the liquid process medium. The result is represented in FIG. 1, wherein the duration of the heat treatment at a given temperature is plotted in minutes along the horizontal x-axis, the semi-quantitative degree of decomposition is indicated as a percentage on the perpendicular z-axis, and the three selected temperatures of 190° C., 210° C., 230° C. and 245° C. are plotted on the y-axis which progresses into the image plane. It is evident that higher rates of decomposition can be achieved more quickly as the temperature increases to 245° C.

EXAMPLE 8—CONTROL EXPERIMENT WITHOUT OVERPRESSURE

In a control experiment, two separate samples, consisting of 2 g TDI polyurethane foam (Product designator: R 4030; Source: Eurofoam Deutschland GmbH Schaumstoffe, Wiesbaden, Germany) and MDI polyurethane foam (Product designator: R 5535; Source: Eurofoam Deutschland GmbH Schaumstoffe, Wiesbaden, Germany) were each reacted with 40 ml 7.5% urea solution and in a glass flask were treated at a temperature from 100° C. to 110° C. under ambient pressure in a heat cabinet, wherein the loss of liquid was supplemented by the addition of water. After 4.5 hours no decomposition of any kind was observed.

EXAMPLE 9—FIRST CONTROL EXPERIMENT WITHOUT UREA, WITH OVERPRESSURE

As a further control experiment, four different samples:
16.6 g black PUR integral foam (window insulation material) in 9.66 ml $H_2O$,
16.6 g white PUR integral foam (component of shoe) in 9.66 ml $H_2O$,
14.0 g PUR semi-hard foam (BASF) in 8.15 ml $H_2O$, and
16.0 g PUR elastomer (Cellasto® from BASF) in 9.66 ml $H_2O$ were each heated for 30 min at 245° C. in closed pressure vessels, wherein the water quantities indicated either contained no urea or 3 mass percent urea.

Figure 2:
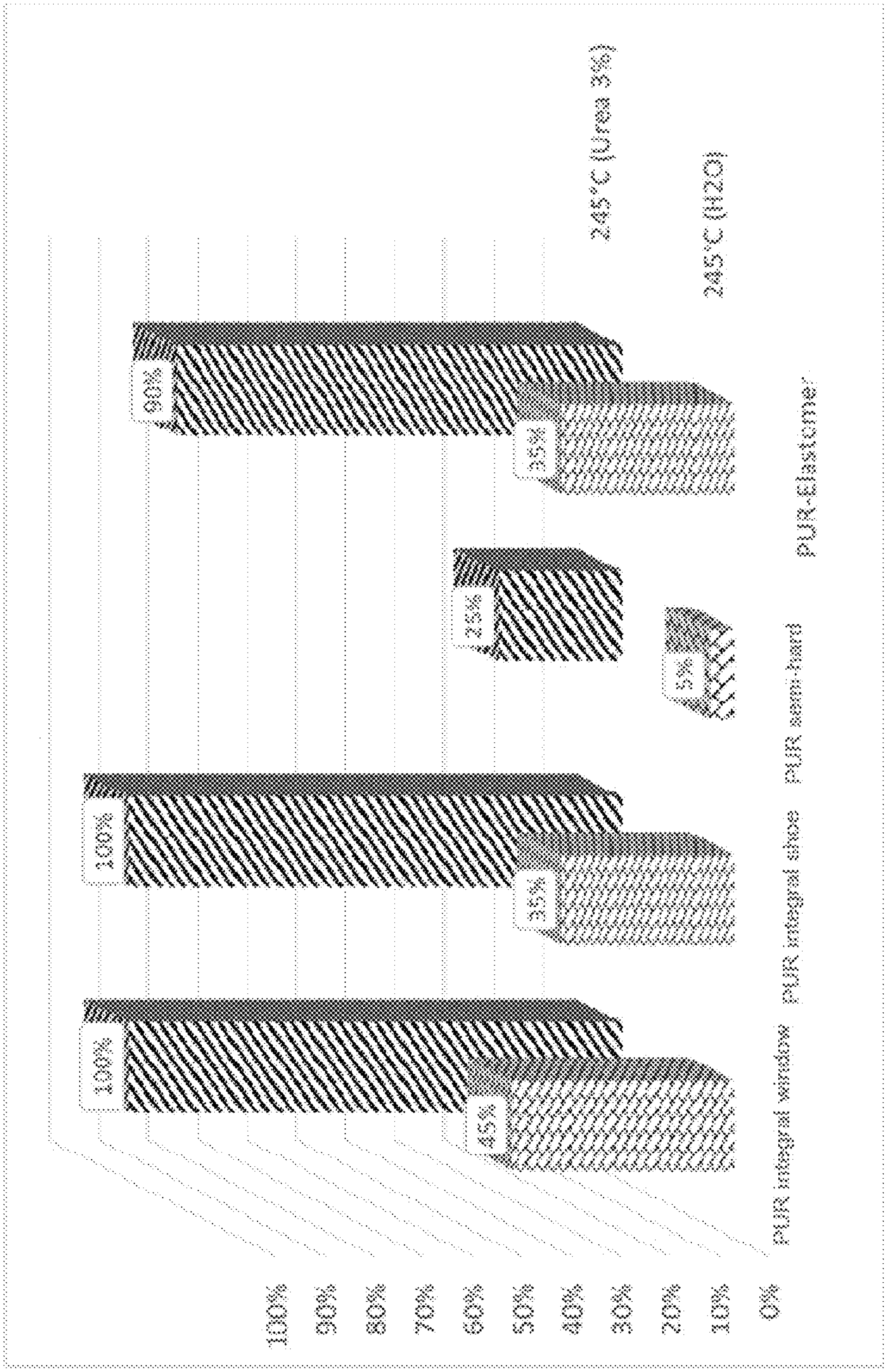
FIG. 2 shows a three-dimensional chart representing the influence of urea on the decomposition of various polyurethane-containing materials for a selected heating duration.

The results are represented in FIG. 2, wherein the samples listed above are identified as “PUR integral window”, “PUR integral shoe”, “PUR-semi-hard” and “PUR elastomer”. The degree of conversion is indicated as a percentage on the y-axis. It was found that in all cases a significant increase in decomposition could be achieved with the addition of urea.

In the case of the integral foams and the elastomer, it was possible to initiate complete or almost complete decomposition of the solid material by this means, and even in the case of the PUR semi-hard foam, which was decomposed less completely after a heat treatment duration of 30 minutes, a clear increased in the rate of decomposition was still recorded following the addition of urea. The less effective decomposition of the semi-hard foam might be caused by poorer heat transfer within the foam material since the semi-hard foam with a volume weight of 133 g/L has considerably lower density than “PUR integral window” (850 g/L), “PUR integral shoe” (790-830 g/L) and “PUR elastomer” (400-550 g/L). To this extent, the PUR semi-hard foam occupied much more space inside the pressure vessel, and was therefore wetted less effectively with the urea-free and the urea-containing aqueous solution, thus making the heat transfer more difficult due to the greater volume of air in the pores.

EXAMPLE 10—SECOND CONTROL EXPERIMENT WITHOUT UREA, WITH OVERPRESSURE

Figure 3:
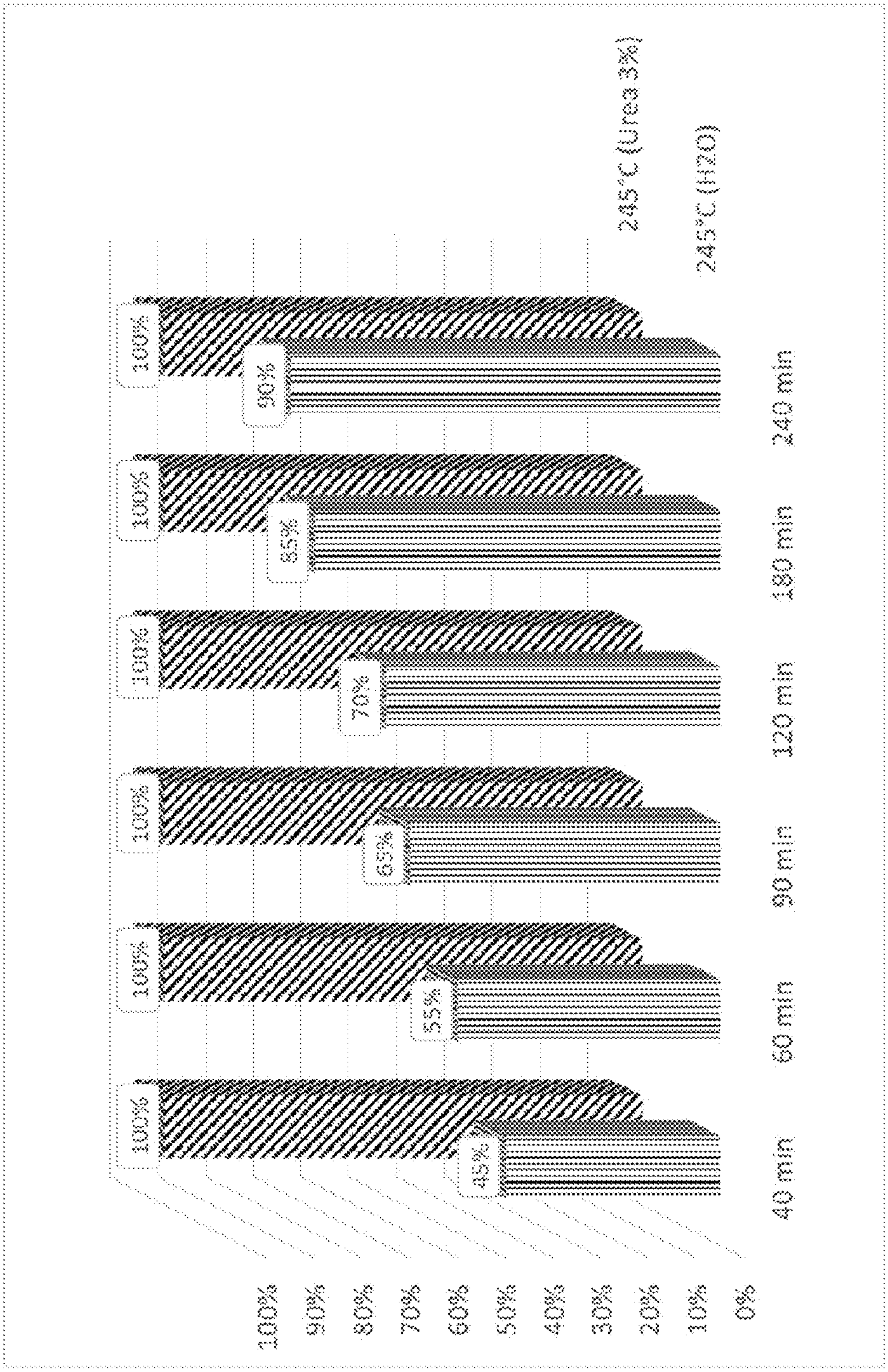
FIG. 3 shows a three-dimensional chart representing the influence of urea on the decomposition of a polyurethane-containing material in a time series.

In a further control experiment, multiple samples of a mixture of polyurethane soft foams (either 16.6 g in 9.66 ml water pr 16.6 g in 9.66 water containing 3 mass percent urea) were heated at 245° C. in closed pressure vessels and removed at different time points (40, 60, 90, 120, 180 and 240 min). Compared with the samples used in Example 9, in terms of material properties the mixture of polyurethane soft foams was most similar to the PUR semi-hard foam. The results are represented in FIG. 3, wherein the time point in minutes is indicated on the x-axis and the degree of conversion in percent is indicated on the y-axis. It was found that in the presence of 3 mass percent urea complete decomposition was recorded after a heating duration of just 40 minutes, whereas in urea-free water only partial decomposition had occurred after 40 minutes, and while this also increased as the heating period progressed, in each case it lay below the decomposition that could be achieved with treatment using urea-containing water.

EXAMPLE 11—EXPERIMENT WITH SIMPLY STRUCTURED SOFT FOAM SYSTEM (SINGLE POLYOL FOAM), ANALYSIS OF PRODUCTS OF DECOMPOSITION

In order to determine the products of decomposition produced after the method was implemented, a polyurethane soft foam with the simplest possible chemical structure was produced in the laboratory (Table 7). In order to maintain a distinction between the influencing factors, only one standard ether polyol with a molecular weight 3500 MW was used, and toluene diisocyanate TDI 80 was implemented as the isocyanate. The volume weight of the foam was 22 kg/m$^3$

TABLE 7

| Raw material | Parts by weight |
|---|---|
| Polyol Standard Ether (3500 MW) | 100 |
| Amin BDE - Dabco BL 11 (Evonik Industries, Essen, Germany | 0.1 |
| Amin TEDA - Dabco 33 LV Evonik Industries, Essen, Germany | 0.22 |
| Silikon Niax L 620 (Momentive Performance Materials, D-Leverkusen | 0.48 |
| Water, metered | 4.48 |
| Tin octoate, pure | 0.15 |
| TDI 80 | 50.81 |

This PUR soft foam was comminuted and processed using the method in a 11.5 litre Büchi reactor (Büchi A G, Uster, Switzerland). 400 gram foam were pre-moistened with 236 millilitres of a 3% water-urea solution and poured into a stainless steel digestion vessel (also called an Inliner vessel) with a volume of about 10.2 litres. The bottom of the vessel was lined with aluminium foil having a rim height of 5 cm to catch the liquid process medium produced. 200 ml water was placed below the Inliner vessel inserted in the reactor in order to generate water vapour rapidly. The method according to the invention was conducted for a period of 240 min, the reactor shell temperature initially being set 260° C. for 60 min, and subsequently to 250° C. for 180 min. By this process, the inner chamber of the reactor reached a temperature of just below 230° C. (229.3° C.).

In order to carry out a chemical analysis of the process medium obtained, 1 ml of the medium was dissolved in 99 ml acetonitrile and mixed on a laboratory vibrating plate for 24 h. Then, the acrylonitrile sample mixture was filtered with a syringe filter (e.g. Chromafil Xtra, RC, 25 mm, 0.45 µm) before 1-5 microlitres of the sample were introduced directly into a gas chromatography system of type Agilent 8890 GC (Agilent, Santa Clara, USA). The GC column was initially maintained for 2 minutes at 40° C., and then warmed from 40° C. to 250° C. at a heating rate of 10 Kelvin per minute. At the end, a hold time of 5 minutes was added. In all, the measurement time lasted 28 minutes. The measurement was taken with a 1:10 split. The method is named Ramp40-250_28 min_1.5 ml_split1-10.M. The spectrum that was measured with the coupled Agilent 5977B GC/MSD mass spectrometer system shows two prominent peaks at retention times 1.37 to 1.75 minutes and 13.71 minutes. The spectra were analysed using the "NIST17" software package, which was included in the scope of delivery of the TG/STA-GC-MS system that is described in greater detail in the context of Example 12 (National Institute of Standards and Technology, Gaithersburg, USA), and also included the "AMDIS32" software for qualitative GC-MS analyses, the databases ALKANES, NISTCW, NIST-DRUG, NISTEPA, NISTFAD, NISTFF, NISTTOX and PESTPLUS, and the MSSEARCH software, wherein this last software program can be used to selectively compare individual measured scans with the databases used. The analysis of the peaks is shown in Table 8, wherein MF (Match Factor) stands for comparing the measured spectrum with the spectra in the databases, and RFM (Reverse Match Factor) means comparing the available database spectra with the measured spectrum. In both cases, a special algorithm stored in the software is used. These factors are standardised to 1000=100% match in the NIST software.

TABLE 8

| Retention time [min] | Substance | MF | RMF |
|---|---|---|---|
| 1.37 | Acetonitrile (CAS 75-05-8) | 897 | 900 |
| 1.75 | Acetonitrile (CAS 75-05-8) | 912 | 914 |
| 13.71 | 1,3-Benzenediamine, 4-methyl-(CAS 95-80-7) | 962 | 963 |

The acetonitrile may be attributed to the solvent used, acetonitrile. A synonym for the 1,3-Benzenediamine, 4-methyl-(CAS 95-80-7) is 2,4-Diaminotoluene. The 2,4-Diaminotoluene peak indicates that this compound can be obtained in the course of the method according to the invention. 2,4-Diaminotoluene is a precursor of toluene diisocyanate TDI 80, into which it can be converted by phosgenation, and thus represents an industrially valuable, reusable raw material, particularly in the context of the polyurethane economy.

A Gel Permeation Chromatography (GPC) analysis was also performed on the process medium to determine its molecular weight (external measurement at BASF Lemförde-Central Analytic Lemförde, BASF Polyurethanes GmbH, Elastogranstr 60, 49448 Lemfoerde, Germany).

In the course of this analysis, a molar mass distribution with a pronounced main peak at 3700 g/mol was measured. The viscosity of the process medium was also determined. It has a value in the order of 1100 mPas. The OH number of the process medium was also determined and found to be 325 mg KOH/g.

The results supported the theory that a substantial component of the process medium is represented by polyol. Its molar mass is very similar to that of the polyol used originally, and (possibly due to the treatment it underwent during the method) has a slightly higher viscosity (Polyol Standard Ether −3500 MW=25 700−900 mPa·s, OH 48) and a higher OH number.

Accordingly, the method according to the invention may be used to recover polyols and return them for reuse as valuable raw materials.

EXAMPLE 12—EXPERIMENT WITH PUR SOFT FOAM MIXTURE, ANALYSIS OF THE PRODUCTS OF DECOMPOSITION BY TG-GC/MS

This example represents an attempt to demonstrate that polyols produced in the course of the method according to the invention were present in the process medium obtained. To this end, the process medium was to be thermally decomposed at temperatures of about 380° C., allowing a statement to be made regarding the presence of polyols in the process medium from the products of decomposition obtained thereby. To do this, the path was chosen via coupled TG/STA-GC-MS measurements (coupling of gas chromatography mass spectrometer with thermal analysis, wherein TG stands for thermogravimetry and STA for "simultaneous thermal analysis"). The measuring instruments used were a STA 449 F3 Jupiter (Netzsch, Selb, Germany) which was connected to the Agilent 8890 GC type gas chromatography system (Agilent, Santa Clara, USA) and the Agilent 5977B GC/MSD mass spectrometer system via a heated transfer line.

First, in a preparatory step, a reference database was created as follows.

For this, the polyols listed in Table 9 below were used, as these represent constituent components of the soft foams used in mixture actually analysed later with reference to the database (see Table 10).

TABLE 9

| Polyol | Suffix in the AMDIS database |
|---|---|
| Standard 3500 MW | STD_POLYOL |
| Standard 45% SAN Polyol | SAN_45% |
| HR 6000 MW Polyol | HR_6000 |
| HR 25% SAN Polyol | HR_SAN |
| HR high functional Polyol | HR_HF |
| Hypersoft Polyol | HYPERSOFT |
| Viscoelastic Polyol | VE8420 |

These were each decomposed individually at 380° C. in the thermal decomposition stage of the TG/STA-GC-MS system described previously. The main peaks were determined with the databases from NIST and AMDIS (see Example 11), and the name of the assigned compound according to these databases and the GC retention times of the decomposition products were stored in the reference database, and the appropriate suffix according to Table 9 was assigned to each decomposition product. If the same decomposition products occurred with different polyols, the respective suffix was added. These decomposition products with the corresponding identifying product code are then listed in Table 11 (wherein in Table 11 the decomposition products of the mixture according to Table 10 are shown).

After the reference database was created, in order to answer the question of the extent to which polyols appear in the process medium after the method according to the invention has been carried out, a mixture of soft foams was subjected to the method according to the invention.

For this purpose, 400 gram of a mixture of soft foams were processed with the method according to the invention in the 11.5 litre Buchi reactor. The mixture had the following soft foam qualities (obtained from Neveon Holding GmbH, Ebersbach-Fils, Germany):

TABLE 10

| Soft foam | Class | Quantity [g] |
|---|---|---|
| N 3045 | TDI 80 - standard | 100 |
| R 4040 | TDI 80 - high resilience | 100 |
| R 5535 | MDI - high resilience | 100 |
| V 5018 | MDI - viscoelastic | 100 |

The 400 grams of foam mixture were pre-moistened with 236 millilitres of a 3% water-urea solution and poured into a stainless steel (volume approx. 10.2 litres). The bottom of the vessel was lined with aluminium foil having a rim height of 5 cm to catch the liquid process medium produced. 200 ml water was placed below the Inliner vessel in order to generate water vapour rapidly.

The method was carried out over a period of 240 min, the reactor shell temperature initially being set 260° C. for 60 min, and subsequently to 250° C. for 180 min. By this process, the inner chamber of the reactor reached a temperature of just under 236° C.

The process medium recovered was again analysed with coupled TG/STA-GC-MS measurements.

The spectrum at 379° C. was analysed with AMDIS and with the reference database created in the preparatory step with a default Minimum Match Factor (MF) setting of 80%. The match factor refers to the agreement between the measured spectrum and the spectra from the AMDIS databases expressed as a percentage. This factor is calculated by algorithms stored in the software. The main peaks correspond to the peaks that were measured for the single polyols according to Table 9. The correlation of this data is presented in Table 11. The analysis result shows that the process medium contains polyols that were used originally as well as conversion products and/or products of decomposition that were produced in the course of the decomposition method.

TABLE 11

| Retention time [min] | Substance | MF |
|---|---|---|
| 2.4464 | Ethanol, 2-methoxy-, acetate_STD_POLYOL (CAS#: 110-49-6)<br>IUPAC: 2-methoxyethyl acetate | 83 |
| 3.9042 | 1-Propene, 2-(1-methylethoxy)_HR_6000 (CAS#: 4188-63-0)<br>IUPAC: (E)-1-propan-2-yloxyprop-1-ene | 93 |
| 6.5138 | Diisopropylether_HR_SAN (CAS#: 108-20-3) | 99 |
| 6.9436 | 2-Propanone, 1-(1-methylethoxy)-_STD_POLYOL_HR_HF_VE8420 (CAS#: 42781-12-4)<br>1-Isopropoxyacetone<br>IUPAC: 1-propan-2-yloxypropan-2-one | 100 |

TABLE 11-continued

| Retention time [min] | Substance | MF |
|---|---|---|
| 7.4102 | Oxirane, trimethyl-__HR__6000 (CAS#: 5076-19-7)<br>Trimethyloxiran<br>IUPAC: 2,2,3-trimethyloxirane | 98 |
| 7.6279 | Carbonic acid, allyl 2-ethoxyethyl ester__HR__6000<br>(NIST#: 357377) (ID#: 2-87-3) | 93 |
| 8.3387 | Styrene__SAN__45%__HR__SAN (CAS#: 100-42-5)<br>Styrol | 97 |
| 9.4547 | Diisopropyl ether__HR__6000__HR__HF (CAS#: 108-20-3) | 99 |
| 9.5666 | 3-Pentanol, 2-methyl-__HR__6000__HR__HF (CAS#: 565-67-3)<br>IUPAC: 2-methylpentan-3-ol | 98 |
| 9.9325 | 2-Pentanone, 5-methoxy-__STD__POLYOL__HR__HF__VE8420 (CAS#: 17429-04-8)<br>IUPAC: 5-methoxypentan-2-one | 89 |
| 10.1310 | Ethanol, 2-(2-ethoxyethoxy)-__HYPERSOFT (CAS#: 111-90-0)<br>Diethylene glycol monoethyl ether | 98 |
| 11.3633 | 1-Propanol, 3-[3-(1-methylethoxy)propoxy]-__STD__POLYOL__HR__SAN__HR__HF<br>(CAS#: 54518-03-5)<br>IUPAC: 3-(3-Isopropoxypropoxy)propan-1-ol | 99 |
| 11.4137 | 1-Propanol, 2-(2-hydroxypropoxy)-__VE8420 (CAS#: 106-62-7)<br>IUPAC: 2-(2-hydroxypropoxy)propan-1-ol | 94 |
| 11.5686 | Propane, 1,1-dipropoxy-__STD__POLYOL__HR__HF<br>(CAS#: 4744-11-0)<br>Dipropylpropylal | 98 |
| 11.9289 | 1-Butoxypropan-2-yl isobutyl carbonate__HR__6000__HR__HF<br>(NIST#: 378276) (ID#: 26899) | 98 |
| 13.0548 | 1-Propanol, 2,2'-oxybis-__STD__POLYOL__VE8420<br>(CAS#: 108-61-2)<br>2,2'-Oxydipropanol | 96 |
| 13.2251 | Ethanol, 2-12-(2-ethoxyethoxy)ethoxy]-__HR__6000__HR__HF<br>(CAS#: 112-50-5)<br>Triethylene Glycol Monoethyl Ether | 83 |
| 13.3345 | 12-Crown-4 HR__6000__VE8420 (CAS#: 294-93-9)<br>1,4,7,10-Tetraoxacyclododecan | 94 |
| 13.9039 | Diethyl carbitol__HYPERSOFT (CAS#: 112-36-7)<br>Diethyler et yylether | 83 |
| 14.2187 | Tri(propylene glycol) propyl ether__STD__POLYOL<br>(CAS#: 96077-04-2) | 81 |
| 14.5563 | 2-Propanol, 1-[1-methyl-2-(2-propenyloxy)ethoxy]-<br>STD__POLYOL__VE8420 (#: 55956-25-7) | 94 |
| 15.5887 | Tripropylene glycol monomethyl<br>ether__STD__POLYOL__VE8420 (<br>CAS#: 20324-33-8) | 81 |
| 16.5011 | Benzene, 1,1'-(1,3-propanediyi)bis-__SAN__45% (CAS#: 1081-<br>75-0)<br>1,3-Diphenylpropan | 89 |
| 17.6774 | 4,8,12,16-tetraoxaeicosan-1-ol__HR__6000__HR__HF<br>(NIST#: 397636) (ID#: 32-16-4)<br>IUPAC: 3-13-[3-(3-butoxypropoxy)propoxy\|propoxy]propan-1-ol | 96 |
| 17.8010 | Pentaethylene glycol__HR__SAN (CAS#: 4792-15-8) | 92 |
| 19.5699 | 3,6,9,12-Tetraoxatetradecan-1-ol__HYPERSOFT (CAS#: 5274-68-0)<br>IUPAC: 2-[2-[2-(2-dodecoxyethoxy)ethoxy]ethoxy]ethanol<br>Tetraethyleneglycol monododecyl ether | 85 |
| 19.5699 | Tetraethylene glycol diethyl ether__HYPERSOFT<br>(CAS#: 4353-28-0)<br>IUPAC: 1-ethoxy-2-12-12-(2-ethoxyethoxyjethoxy ethoxyjethane<br>3,6,9,12,16-Pentaoxaheptadecane | 85 |
| 19.5988 | 1,4,7,10,13,16-Hexaoxacyclooctadecane<br>HYPERSOFT__HR__6000 (CAS#: 17455-13-9)<br>18-Crown-6 ether | 84 |
| 19.6542 | 3-Phenylpropanol__SAN__45% (CAS#: 122-97-4)<br>IUPAC: 3-phenylpropan-1-ol<br>Benzenepropanol | 81 |
| 19.9315 | (1-Benzyl-2-O-tolyl-ethyl)-isonitrile__SAN__45%<br>(NIST#: 287385), (ID#: 88-42-6)<br>IUPAC: N-11-(2-methylphenyl)-3-phenylpropan-2-yl]methanimine | 82 |

The spectrum at 265° C. was analysed with AMDIS and with the databases of AMDIS and NIST with a default Minimum Match Factor (MF) setting of 90%. In prior experiments, it was discovered that at a temperature of 265° C. the components contained in the process medium that can be traced back to the diisocyanate in the polyurethane are broken down thermally, while components in the polyurethane that can be traced back to the polyols are not broken down at this temperature.

The main peaks correspond to the diamine precursors of the diisocyanates used in the soft foams (Table 12). The liquid process medium obtained after the method according to the invention has been carried out thus contains the precursors from before the industrial step of phosgenation of the diisocyanates.

TABLE 12

| Retention time [min] | Substance | MF |
|---|---|---|
| 9.7657 | Aniline | 99 |
| 14.2512 | 1,3-Benzenediamine, 4-methyl- | 98 |
| 14.2727 | 1,3-Benzenediamine, 4-methyl- | 98 |
| 18.9949 | Benzenamine, 4,4'-methylenebis- | 92 |
| 19.4296 | Benzenamine, 4,4'-methylenebis- | 100 |
| 19.8471 | Benzenamine, 4,4'-methylenebis- | 98 |

The described method enables the of decomposition polyurethane and is therefore commercially applicable. Moreover, raw materials can be recovered from the process medium obtained, and these may be used again in the chemical industry, in particular they are useful to the polyurethane-recycling economy.

Although the invention has been illustrated and explained in greater detail with the aid of preferred embodiments thereof, the invention is not limited by the disclosed examples, and other variations may be derived therefrom by the person skilled in the art without departing from the scope of protection of the invention. It is therefore evident that a multiplicity of variation possibilities exist, and that the variants identified, or elements thereof, can be combined with each other. It is also evident that variants identified for exemplary purposes really do only represent examples, which are not to be interpreted in any way as constituting a limitation of the range of protection, the application possibilities or the configuration of the invention. Rather, the preceding description and the description of the figures are designed to enable the person skilled in the art to reproduce the exemplary embodiments in concrete terms, wherein the person skilled in the art with knowledge of the disclosed inventive thought is able to introduce many changes, for example with regard to the function or arrangement of individual elements identified in an exemplary variant without departing from the scope of protection of the invention, which is defined by the claims and their legal counterparts, such as more detailed explanations in the description.

The invention claimed is:

1. A method for decomposing polyurethane, wherein a polyurethane-containing material is heated to a temperature from 190° C. to 250° C. under overpressure in the presence of an aqueous solution containing 1 to 45 mass percent urea.

2. The method according to claim 1, wherein heating takes place under a pressure from 1.05 bar to 100 bar.

3. The method according to claim 1, wherein the overpressure is an equilibrium pressure established upon heating.

4. The method according to claim 1, wherein the heating takes place over a period from 20 minutes to 240 minutes.

5. The method according to claim 1, wherein the aqueous solution comprises 2.5-10 mass percent urea, and the heating takes place over a period from 45-250 min.

6. The method according to claim 1, wherein the ratio between urea-containing aqueous solution and polyurethane-containing material has a value from 0.4 ml/g to 5 ml/g.

7. The method according to claim 1, wherein after heating at least some of the liquid process medium obtained is recovered.

8. The method according to claim 7, characterized in that solids are removed from the recovered liquid process medium.

9. The method according to claim 1, wherein the aqueous solution is free from polyols and/or free from carboxylic acid and/or free from ammonia.

10. The method according to claim 1, wherein the aqueous solution consists of water and urea.

11. A liquid process medium, obtainable with a method according to claim 1, wherein the heating takes place at a temperature from 190° C. to 250° C. over a period from 20 minutes to 240 minutes, wherein the aqueous solution contains 1 to 10 mass percent urea and the ratio between urea-containing aqueous solution and polyurethane-containing material has a value from 0.4 ml/g to 5 ml/g.

* * * * *